United States Patent

Auer et al.

[11] Patent Number: 6,048,441
[45] Date of Patent: Apr. 11, 2000

[54] ISOLATION OF NEOPENTYL GLYCOL HYDROXYPIVALATE (NGH)

[75] Inventors: Heinz Auer, Neulussheim; Siegfried Krüger, Speyer; Stephan Scholl, Bad Dürkheim; Theodor Weber, Ludwigshafen; Johann-Peter Melder, Neuhofen, all of Germany

[73] Assignee: BASF Aktiengesellschaft, Ludwigshafen, Germany

[21] Appl. No.: 09/121,865

[22] Filed: Jul. 24, 1998

[30] Foreign Application Priority Data

Aug. 5, 1997 [DE] Germany .............................. 197 33 903

[51] Int. Cl.⁷ .............................. B01D 3/14; C07C 69/675
[52] U.S. Cl. .............................. 203/72; 203/74; 203/75; 203/77; 203/78; 203/80; 203/99; 203/DIG. 19; 560/179; 159/6.2
[58] Field of Search .............................. 560/179, 186; 203/72, 75, 77, 78, 87, 94, 80, 99, DIG. 19; 159/6.2

[56] References Cited

U.S. PATENT DOCUMENTS

| 3,641,118 | 2/1972 | Platz et al. | 260/484 |
|---|---|---|---|
| 3,696,005 | 10/1972 | Fuchs | 203/35 |
| 3,769,177 | 10/1973 | Eubanks et al. | 203/71 |
| 3,852,335 | 12/1974 | Merger et al. | 260/484 |
| 3,878,029 | 4/1975 | Baird et al. | 159/6 |
| 4,665,219 | 5/1987 | Merger et al. | 560/189 |
| 4,935,555 | 6/1990 | Elias et al. | 568/854 |
| 5,209,827 | 5/1993 | Butler et al. | 203/72 |

FOREIGN PATENT DOCUMENTS

| 410 167 | 1/1991 | European Pat. Off. . |
|---|---|---|
| 555 335 | 8/1993 | European Pat. Off. . |

*Primary Examiner*—Rosalynd Keys
*Attorney, Agent, or Firm*—Keil & Weinkauf

[57] ABSTRACT

Neopentyl glycol hydroxypivalate (NGH) is isolated from a mixture containing NGH, lower- and higher-boiling products and inorganic salts and purified in a two-stage process, wherein in a first separation stage, the inorganic salts and part of the higher-boiling products are separated off in a wiped-film evaporator and a vapor stream consisting of NGH, lower- and higher-boiling products is discharged and fed to a heat exchanger and condensed therein, and, in a second separation stage, the resulting condensate is distilled in a rectification column from which NGH is taken off in a side stream and condensed. Further discharges of the rectification column containing lower-boiling products or higher-boiling products are separately taken off. The higher-boiling products which comprise residual NGH are partly or completely recycled to the lower region of the rectification column.

10 Claims, 1 Drawing Sheet

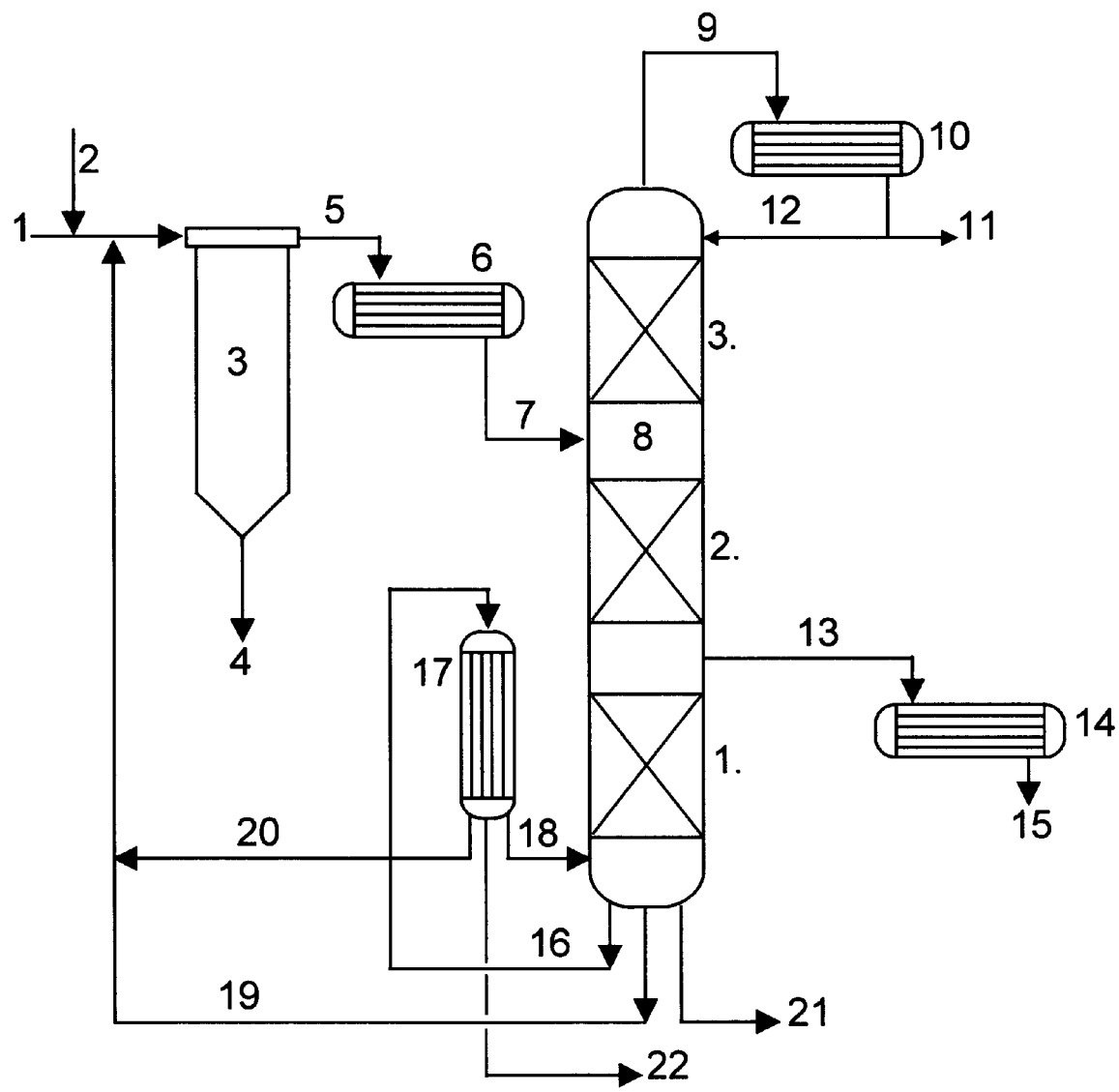

ISOLATION OF NEOPENTYL GLYCOL HYDROXYPIVALATE (NGH)

The invention relates to a process for isolating neopentyl glycol hydroxypivalate (NGH) from a mixture containing NGH, lower- and higher-boiling products and inorganic salts. The invention additionally relates to an apparatus for carrying out the process.

Neopentyl glycol hydroxypivalate (NGH), also called hydroxypivalyl hydroxypivalate, is prepared industrially for example by the Tishchenko reaction from hydroxypivalaldehyde in the presence of basic inorganic catalysts. The hydroxypivalaldehyde in this case is prepared, for example, from isobutyraldehyde and formaldehyde. The NGH prepared in this way may contain relatively large amounts of impurities such as isobutyraldehyde, isobutanol, unreacted hydroxypivalaldehyde, neopentyl glycol and neopentyl glycol monoisobutyrate, in addition to the high-boiling products and residues of inorganic catalysts. Some of the impurities may have been introduced together with the hydroxypivalaldehyde employed in the reaction.

NGH is a thermally sensitive substance which begins to decompose on prolonged heating at high temperatures, in particular above 150° C. Purification of NGH by thermal processes such as distillation is difficult for this reason. Attempts must be made to minimize the thermal stress.

Various processes for purifying this crude NGH mixture have been described.

U.S. Pat. No. 3,641,118 and U.S. Pat. No. 3,696,005 describe processes for purifying NGH using acids or acidic ion exchangers. For example, distillation in the presence of an acid is carried out.

To remove salts such as calcium hydroxide, barium hydroxide or strontium hydroxide, it has been proposed in U.S. Pat. No. 4,665,219 to adjust the water content of the reaction mixture to 20–60% and to extract the salt at from 50 to 100° C.

EP-A1-0 410 167 describes a process for preparing NGH and eutectic mixtures of neopentyl glycol and NGH from the by-product stream from a preparation of neopentyl glycol. The reaction product can be distilled using a wiped-film evaporator and a series of condensers, it being possible to remove NGH by another distillation process which is not precisely specified.

U.S. Pat. No. 4,935,555 describes a process for preparing neopentyl glycol wherein a sodium hydroxide solution is added to the crude product, which is purified using a wiped-film evaporator. The wiped-film evaporator can moreover be connected to a column, from which low boilers are taken overhead, high boilers from the bottom and neopentyl glycol as sidestream. The bottom product from the wiped-film evaporator is moreover fed to a decanting apparatus. EP-B1-0 555 335 describes a process for isolating hydroxypivalyl hydroxypivalate from a crude synthetic mixture in which the mixture is fed to a wiped-film evaporator in a first distillation unit where inorganic salts and high-boiling constituents are removed as bottom product. The distillate is fed to a partial condensate column where high-boiling constituents are condensed. The vapors of NGH and low-boiling products obtained from the partial condensate column are fed to a low-boiler column in a second distillation unit. The low-boiling products are removed overhead from the low-boiler column and are condensed, it being possible to recycle part of the condensate to the top of the column. The bottom product from the column is fed to a second wiped-film evaporator from whose distillate NGH is removed. A remaining distillate fraction can be recycled to the column. High-boiling products are removed from the bottom product of the second wiped-film evaporator. These products can be taken off as residue or recycled to the first wiped-film evaporator. One disadvantage of this process is the need to use two wiped-film evaporators, which are very costly. In addition, the first distillation unit is pressure-coupled to the second distillation unit and cannot be operated under independent process conditions. This makes the process difficult to control and sensitive to disruptions and fluctuations. In addition, as a rule, two residue streams are produced from the two wiped-film evaporators.

Another disadvantage is that the pure NGH cannot be completely separated from high-boiling impurities which boil close to the NGH boiling point, because there is only a one-stage evaporation, and no rectification, between removal of high boilers in the second wiped-film evaporator and the taking off of pure NGH.

It is an object of the present invention to provide a process for isolating NGH from a mixture containing NGH, lower- and higher-boiling products and inorganic salts, which allows very pure NGH to be prepared in high yield and without colored impurities, the process being less complicated than known processes, permitting good control of the individual stages in the process, and not being susceptible to disruptions.

We have found that this object is achieved by a process for isolating neopentyl glycol hydroxypivalate (NGH) from a mixture containing NGH, lower- and higher-boiling products and inorganic salts, which comprises the mixture being, in a first separation stage consisting of a wiped-film evaporator and a heat exchanger, fed to the wiped-film evaporator, in which a stream of higher-boiling products and inorganic salts is discharged as bottom product and in which a distillate stream consisting of NGH, lower- and higher-boiling products is discharged and fed to the heat exchanger and condensed therein, and the resulting condensate stream being, in a second separation stage consisting of a rectification column for separating NGH, lower- and higher-boiling products, a second evaporator and heat exchangers, fed to the column, in which a distillate stream consisting of low-boiling products is discharged and condensed in a heat exchanger, the resulting condensate is, where appropriate, partly recycled to the rectification column and partly taken off as low-boiler stream, a distillate sidestream of NGH is discharged and condensed in a heat exchanger a bottom stream of NGH and higher-boiling products is discharged and at least partly fed to the second evaporator, with all or part of the discharge from the evaporator being recycled to the lower region of the column.

It has been found according to the invention that using a heat exchanger for complete condensation of the distillate from the wiped-film evaporator in the first separation stage and feeding the liquid condensate to the second separation stage makes pressure decoupling of the two stages possible. This means that the pressures in the two separation stages can be chosen without restriction, and thus the process conditions can be adjusted more flexibly. Disruptions and process fluctuations, such as pressure fluctuations, have an effect only on the corresponding separation stage but not on the overall process. If there are disruptions, the two separation stages can be taken out of operation independently of one another.

In addition, in the process disclosed in EP-B1-0 555 335 it is necessary in the partial condensate column for a number of parameters to be maintained accurately in order to ensure removal of high-boiling products at this point. Thus, the temperature must be in the range from 150 to 175° C., a pressure of from 5 to 30 Torr must prevail and, at the same time, at the top of the column the temperature must be lower by 1–5° C. and the pressure must be lower by 1–5 Torr than at the base of the column. Only under these conditions is it ensured that no higher-boiling products reach the second distillation zone, where removal thereof is no longer possible because only a one-stage evaporation takes place in the second wiped-film evaporation. Particularly critical in this connection are higher-boiling impurities with a boiling point higher than, but close to, the boiling point of pure NGH, like all condensation products. These can be separated efficiently from pure NGH only by utilizing the rectification effect.

The removal of high-boiling products takes place according to the invention in the first wiped-film evaporator in the first separation stage, as well as in the rectification column in the second separation stage. This makes it possible after the first wiped-film evaporator to operate a heat exchanger, in which the process conditions are non-critical, for complete condensation.

It is additionally possible in the process according to the invention to employ as second evaporator in the second separation stage any suitable evaporator which permits evaporation of the bottom product with low thermal stress. The evaporator serves to produce vapors for the rectification column, ie. to provide the vapor stream for rectification of the mixture of substances to be separated in the column. NGH is purified in the column by removal as sidestream from the column above the first separation section. As disclosed in EP-B1-0 555 335, the purification and removal of NGH are effected by the second wiped-film evaporator which thus serves not only to produce vapors but also to purify NGH by evaporation and to allow a residue stream of high-boiling products to be removed.

BRIEF DESCRIPTION OF DRAWING

Preferred embodiments of the invention are explained below by means of the drawing which shows in FIG. 1 a diagrammatic representation of the process according to the invention,
where the meanings are:
: first separation section
: second separation section
: third separation section
(1): crude NGH mixture feed
(2): fluidifier feed
(3): wiped-film evaporator in the first separation stage
(4): bottom product from the wiped-film evaporator (3)
(5): feed of distillate from the wiped-film evaporator (3) to the heat exchanger (6)
(6): heat exchanger
(7): feed from heat exchanger (6) to the column (8)
(8): rectification column
(9): feed from top of column (8) to heat exchanger (10)
(10): heat exchanger
(11): take-off of distillate from heat exchanger (10)
(12): return to column (8)
(13): sidestream from column (8)
(14): heat exchanger
(15): outlet from heat exchanger (14)
(16): recycle stream to evaporator (17)
(17): evaporator in the second separation stage
(18): feed from evaporator (17) to bottom of the column (8)
(19): feed from bottom of column (8) to the wiped-film evaporator (3) in the first separation stage
(20): feed from evaporator (17) to the wiped-film evaporator (3) in the first separation stage
(21): outlet from the bottom of column (8)
(22): outlet from the evaporator (17)

The mixture (1) of NGH, lower- and higher-boiling products and inorganic salts which is fed to the wiped-film evaporator (3) preferably contains 75–85% by weight NGH, 15–25% by weight lower-boiling products, 0.1–2.0% by weight higher-boiling products and 0.1–2.0% by weight inorganic salts, where the total of the constituents is 100% by weight. Lower-boiling products are those whose boiling point is below that of NGH (160° C. under 10.5 mbar). Examples of such products are hydroxypivalic acid (HPA), isobutyraldehyde, isobutanol, formaldehyde, hydroxypivalaldehyde (HPA), neopentyl glycol, neopentyl glycol monoisobutyrate and neopentyl glycol monoformate.

Higher-boiling products are those products whose boiling point is higher than that of NGH. Examples thereof are higher condensation products of NGH with hydroxypivalic acid or isobutyric acid and isomeric condensation products of NGH with formic acid.

Inorganic salts are mainly the basic inorganic catalysts employed for preparing NGH, in particular alkaline earth metal hydroxides such as calcium hydroxide, barium hydroxide or strontium hydroxide.

In a preferred embodiment of the invention, a high-boiling compound which is inert under the processing conditions and towards the products of the process is added as fluidifier (2) to the (crude NGH) mixture described above. This fluidifier has the task of preventing adhesion of inorganic salts which precipitate in the first wiped-film evaporator. The boiling point of the fluidifier is therefore so high that it is not evaporated in the wiped-film evaporator but forms part of the bottom product. Suitable fluidifiers are polyethers (with alkylated end groups —OR) and polyetherdiols (with hydroxyl end groups), particularly preferably polyethylene glycol with an average molecular weight of 400 to 600 g/mol. The fluidifier is preferably employed in an amount of from 0.2 to 3.0% by weight based on the feed (1) as 100% by weight. Particularly preferred amounts are in the range from 0.2 to 1.0% by weight. It is possible by use of the fluidifier in the wiped-film evaporator to achieve very substantial evaporation of the vaporizable compounds in the crude NGH mixture employed without preventing the wetting of the heat-transfer surfaces of the wiped-film evaporator. The vaporization efficiency can in this way be increased and the thermal stress on the NGH can be reduced so that thermal degradation of NGH in the evaporator is avoided.

It is possible to use as wiped-film evaporator any suitable evaporator in which the film is mechanically moved by a system of wiper blades. This system may have rigid or movable wiper blades. It is particularly preferred to employ a wiped-film evaporator with movable wiper blades. The evaporator in the first separation stage is preferably operated under a pressure of from 2 to 15, particularly preferably 5 to 10, mbar, and at a jacket temperature of, preferably, 140 to 200° C., particularly preferably 160 to 180° C. The bottom product comprises inorganic salts and highboiling products. When fluidifiers are used, these likewise form part of the bottom product (3).

The distillate (5) from the wiped-film evaporator is fed to a heat exchanger (6) in which the distillate is condensed, preferably as completely as possible. Suitable heat exchangers in this case are all designs of condensers which can be employed industrially. The pressure in the heat exchanger is preferably from 2 to 15, in particular 5 to 10, mbar, and the temperature is preferably 30 to 130, particularly preferably 55 to 110° C. The distillate (5) in this case comprises predominantly NGH and low- and high-boiling products, which are fed, completely or nearly completely condensed, to the column (8).

The column is equipped with suitable internals for separating NGH, low- and higher-boiling products. Internals with a low pressure drop are particularly suitable in the separation section, preferably structured or ordered packings. The column and its internals are moreover preferably designed in such a way that the overhead product comprises low-boiling products, NGH vapor is taken off as sidestream, and the bottom product comprises NGH and higher-boiling products. The rectification column preferably has at least three separation sections, see FIG. 1. The sidestream (13) is removed between the first and second separation sections, and the feed (7) from the heat exchanger (6) preferably takes place between the second and third separation sections.

The specific combination of separation sections makes it possible to obtain NGH in very high purity. It is even separated from impurities boiling only slightly higher. This high purity of the products can be achieved reliably even in the event of disruptions or fluctuations, for example in the composition of the crude NGH and in the condensate fed in from the first separation stage, or if the amount fed in is altered.

The column preferably has 6 to 20, particularly preferably 10 to 14, theoretical plates. Moreover the first separation section preferably has 2 to 6, in particular 3 to 5, theoretical plates, the second separation section preferably has 3 to 9, particularly preferably 4 to 7, theoretical plates and the third separation section preferably has 2 to 6, particularly preferably 3 to 5, theoretical plates. The column may also have other separation sections. It is preferred to use three separation sections. The pressure at the top of the column is from 3 to 20 mbar, preferably 4 to 15 mbar, particularly preferably 5 to 10 mbar. The temperature of the column at the bottom is preferably 150 to 180, particularly preferably about 165 to 175° C., between the first and second separation sections and/or the second and third separation sections is preferably 150 to 170, particularly preferably 155 to 165° C., and at the top is preferably 90 to 100, particularly preferably 93 to 97° C. The temperature of the heat exchanger for condensing the NGH sidestream is preferably 30 to 130, particularly preferably 55 to 110° C.

The low-boiling products obtained as column distillate and condensed can be removed from the process and be re-used or disposed of. If there is a high content of HPA or other precursors from the NGH synthesis, they can, if required after further purification, be recycled in the synthesis. Part or all of the condensate stream can also be recycled to the top of the column. The reflux ratio, ie. the ratio of recycled condensate stream (12) to removed condensate stream (11), is preferably more than 5, particularly preferably 5 to 25, in particular 10 to 20.

In the first separation section, higher-boiling impurities are concentrated in the NGH. The bottom product from the column (8) is used partly as recycle stream (16) to the evaporator (17) and partly as high-boiler discharge. The latter is preferably recycled (19) to the wiped-film evaporator (3). Alternatively, it may also be discharged as residue stream (21). The recycle stream (20) which is rich in high boilers may also, as alternative to stream (19), be removed from the nonvaporized liquid stream from the evaporator (17). This corresponds to separation of the bottom product as described in DE-A-33 38 488. Similar to stream (21), the high boilers can be removed as stream (22) from the nonvaporized liquid in the evaporator (17). The streams (4), (21) and (22) can be disposed of or fed to further processing.

The pure NGH (15) obtained as sidestream preferably has an NGH content of more than 98% by weight, a hazen color number of less than 10 APHA, a water content of less than 0.3% by weight and an acid number of less than 5. A liquid stream from the evaporator in the second separation stage can be recycled to the wiped-film evaporator in the first separation stage.

A liquid stream from the evaporator in the second separation stage can be discharged.

When carrying out the process according to the invention, the streams are preferably employed or controlled in the following amounts:

If the crude NGH feed (1) is fixed at 100% by weight, then the feed stream (2) with fluidifier amounts to 0.5 to 4% by weight, preferably 1 to 2% by weight. The bottom product (4) from the wiped-film evaporator (3) amounts to 1 to 10% by weight, preferably 2 to 8% by weight, particularly preferably 2 to 6% by weight. The ratio of the recycled stream to the fresh feed (19)/(1) or (20)/(1) is 0 to 30%, preferably 5 to 20%, particularly preferably 10 to 20%. 5 to 30%, preferably 10 to 20%, based on stream (1), are taken off as low boilers (11). The take-off of pure NGH (13) is 70 to 95% by weight, preferably 75 to 90% by weight, based on stream (1).

The invention also relates to an apparatus for carrying out the process according to the invention, comprising a first separation stage consisting of a wiped-film evaporator (3) and a heat exchanger (6) and a second separation stage consisting of a rectification column (8), two heat exchangers (10, 14) and a second evaporator (17)

with a feed (1) to the wiped-film evaporator (3), a feed (2) of fluidifier to the wiped-film evaporator (3), an outlet (4) from the wiped-film evaporator (3), a feed (5) for distillate from the wiped-film evaporator (3) to the heat exchanger (6), a feed (7) from the heat exchanger (6) to the column (8), a feed (9) for distillate from the column to the heat exchanger (10), a discharge (11) from the heat exchanger (10), a feed (12) from the heat exchanger (10) to the top of column (8), a side discharge (13) from column (8) to the heat exchanger (14), an outlet (15) from the heat exchanger (14), a discharge (16) from the bottom of column (8) to the second evaporator (17), a feed (18) from the bottom of the second evaporator (18) to the lower part of column (8), a feed (19) from the bottom of column (8) to the wiped-film evaporator (3) in the first separation stage, a feed (20) from the second evaporator (17) to the wiped-film evaporator (3) in the first separation stage, an outlet (21) from the bottom of column (8), an outlet (22) from the second evaporator (17).

EXAMPLE

A stream (1) with the approximate composition 80% by weight NGH, 18% by weight low boilers, 1.8% by weight high boilers and 0.2% by weight inorganic salts is fed into an apparatus like that shown in FIG. 1. Based on (1), 2.0% by weight polyethylene glycol (P 600) is fed as fluidifier in stream (2) to a wiped-film evaporator with movable wiper elements (3). The wiped-film evaporator is operated under a pressure of about 6 to 8 mbar with a jacket temperature of 180° C. The bottom product (4) discharged from the evaporator comprises polyethylene glycol, high boilers and inorganic salts in an amount totaling about 4% based on stream (1). The vaporized product stream is condensed at 50° C. in the heat exchanger (6) and fed to the rectification column (8). The column has an overhead pressure of 6 to 8 mbar with the bottom at about 160° C., the sidestream at from 146 to 155° C., the condensate feed at from 100 to 105° C. and an overhead temperature of from 95 to 97° C. With a reflux ratio of (12)/(11)=15, 17% of stream (1) are discharged as overhead product (11). Pure NGH is discharged as sidestream in an amount of about 80% based on stream (1), and is condensed in a heat exchanger (14) at from 50 to 60° C. The evaporator (17) in the second separation stage is a falling film evaporator operated at from 170 to 180° C. About 10%, based on stream (1), of bottom product (19) from the column is recycled to the wiped-film evaporator (3) in the first separation stage. The sidestream comprises pure NGH with a content of more than 98%, a Hazen color number of less than 10 APHA, a water content of less than 0.3% and an acid number of less than 5. Discharges (20), (21) and (22) are not in operation.

The process according to the invention thus makes it possible to purify NGH under mild conditions so that a high proportion of very pure NGH can be isolated.

We claim:

1. A process for isolating neopentyl glycol hydroxypivalate (NGH) from a mixture containing NGH, lower- and higher-boiling products and inorganic salts, which comprises,
   in a first separation stage,
   $a_1$) feeding the mixture to a wiped-film evaporator,
   $a_2$) separating the mixture into
     a stream of high-boiling products and inorganic salts and
     a distillate stream consisting of NGH, lower- and higher boiling products,
   $a_3$) feeding the distillate stream to a heat exchanger and condensing it to form a liquid condensate,
   and, in a second separating stage,
   $b_1$) feeding the liquid condensate to a rectification column,
   $b_2$) separating the liquid condensate into
     a distillate stream consisting of lower-boiling products,
     a sidestream of NGH, and
     a bottom stream of NGH and higher-boiling products,
   $b_3$) feeding the distillate stream consisting of lower-boiling products to a second heat exchanger and condensing it to form a low-boiling condensate,
   $b_4$) feeding the sidestream to a third heat exchanger and condensing the NGH,
   $b_5$) feeding at least a part of the bottom stream to a second evaporator, and
   $b_6$) recycling at least a part of the discharge from the second evaporator to the lower region of the rectification column.

2. The process defined in claim 1, wherein the rectification column has at least three separation sections one above the other, which can be equipped with internals with a low pressure drop, and wherein the sidestream is taken off between the first and the second separation sections, and the liquid condensate is fed to the rectification column between the second and third separation sections.

3. The process defined in claim 1, which further comprises recycling at least a part of the bottom stream to the wiped-film evaporator.

4. The process defined in claim 1, which further comprises recycling a liquid discharge from the second evaporator to the wiped-film evaporator.

5. The process defined in claim 1, wherein the low-boiling condensate is at least partly recycled to the top of the rectification column.

6. The process defined in claim 1, wherein the second evaporator is a falling film evaporator or a thin-film evaporator.

7. The process defined in claim 1, wherein the mixture employed further comprises a high-boiling fluidifier.

8. The process defined in claim 1, wherein one or more of the following features are implemented in the first separation stage:
   a pressure in the wiped-film evaporator of from 2 to 15 mbar,
   a jacket temperature of the wiped-film evaporator of from 140 to 200° C.,
   a pressure in the heat exchanger of from 2 to 15 mbar,
   a temperature in the heat exchanger of from 30 to 130° C.

9. The process defined in claim 1, wherein one or more of the following features are implemented in the second separation stage:
   a temperature of the liquid condensate of from 30 to 130° C.,
   a bottom temperature of the rectification column of from 150 to 180° C.,
   a temperature at the top of the rectification column of from 90 to 100° C.,
   a temperature of the sidestream NGH condensate of from 30 to 130° C.,
   a temperature in the second evaporator of from 140 to 200° C.,
   the sidestream has an NGH content of more than 98% by weight, a hazen color number of less than 10 APHA, a water content of less than 0.3% by weight and an acid number of less than 5.

10. The process defined in claim 2, wherein one or more of the following features are implemented in the second separation stage:
    a temperature of the liquid condensate of from 30 to 130° C.,
    a bottom temperature of the rectification column of from 150 to 180° C.,
    a temperature between the first and second separation sections of from 150 to 170° C.,
    a temperature between the second and third separation sections of from 150 to 170° C.,
    a temperature at the top of the rectification column of from 90 to 100° C.,
    a temperature of the sidestream NGH condensate of from 30 to 130° C.,
    a temperature in the second evaporator of from 140 to 200° C.,
    the sidestream has an NGH content of more than 98% by weight, a hazen color number of less than 10 APHA, a water content of less than 0.3% by weight and an acid number of less than 5.

* * * * *